(12) United States Patent
Gelbart et al.

(10) Patent No.: US 9,987,084 B2
(45) Date of Patent: *Jun. 5, 2018

(54) APPARATUS AND METHOD FOR INTRA-CARDIAC MAPPING AND ABLATION

(71) Applicant: Kardium Inc., Burnaby (CA)

(72) Inventors: Daniel Gelbart, Vancouver (CA); Samuel Victor Lichtenstein, Vancouver (CA)

(73) Assignee: KARDIUM INC., Burnaby (CA)

( * ) Notice: Subject to any disclaimer, the term of this patent is extended or adjusted under 35 U.S.C. 154(b) by 407 days.

This patent is subject to a terminal disclaimer.

(21) Appl. No.: 14/804,924

(22) Filed: Jul. 21, 2015

(65) Prior Publication Data

US 2015/0351837 A1 Dec. 10, 2015

Related U.S. Application Data

(63) Continuation of application No. 13/785,931, filed on Mar. 5, 2013, now Pat. No. 9,119,633, which is a
(Continued)

(51) Int. Cl.
*A61B 18/08* (2006.01)
*A61B 18/12* (2006.01)
(Continued)

(52) U.S. Cl.
CPC .......... *A61B 18/1492* (2013.01); *A61B 5/015* (2013.01); *A61B 5/027* (2013.01);
(Continued)

(58) Field of Classification Search
CPC . A61B 5/1076; A61B 5/1077; A61B 5/14503; A61B 5/1491; A61B 5/4887;
(Continued)

(56) References Cited

U.S. PATENT DOCUMENTS

| 4,114,202 A | 9/1978 | Roy et al. |
|---|---|---|
| 4,164,046 A | 8/1979 | Cooley |

(Continued)

FOREIGN PATENT DOCUMENTS

| CN | 101797181 A | 8/2010 |
|---|---|---|
| EP | 0723467 A1 | 7/1996 |

(Continued)

OTHER PUBLICATIONS

Non-Final Office Action issued in U.S. Appl. No. 14/229,250 dated Apr. 28, 2016.
(Continued)

*Primary Examiner* — Ronald Hupczey, Jr.
(74) *Attorney, Agent, or Firm* — Rossi, Kimms & McDowell LLP

(57) ABSTRACT

An intra-cardiac mapping system is based on locating the ports through which blood flows in or out the heart chambers. For many procedures, such as ablation to cure atrial fibrillation, locating the pulmonary veins and the mitral valve accurately allows to perform a Maze procedure. The location of the ports and valves is based on using the convective cooling effect of the blood flow. The mapping can be performed by a catheter-deployed expandable net or a scanning catheter. The same net or catheter can also perform the ablation procedure.

15 Claims, 8 Drawing Sheets

Related U.S. Application Data continuation-in-part of application No. 11/475,950, filed on Jun. 28, 2006, now Pat. No. 8,920,411.

(51) Int. Cl.

| | | |
|---|---|---|
| *A61B 5/028* | (2006.01) | |
| *A61B 5/00* | (2006.01) | |
| *A61B 5/029* | (2006.01) | |
| *A61B 18/10* | (2006.01) | |
| *A61B 18/14* | (2006.01) | |
| *A61B 5/01* | (2006.01) | |
| *A61B 5/0205* | (2006.01) | |
| *A61B 5/027* | (2006.01) | |
| *A61B 34/00* | (2016.01) | |
| *A61B 90/00* | (2016.01) | |
| *A61B 18/00* | (2006.01) | |
| *A61B 18/18* | (2006.01) | |
| *A61B 18/20* | (2006.01) | |
| *A61B 18/02* | (2006.01) | |
| *A61B 34/10* | (2016.01) | |

(52) U.S. Cl.
CPC .......... *A61B 5/028* (2013.01); *A61B 5/02055* (2013.01); *A61B 5/6858* (2013.01); *A61B 5/743* (2013.01); *A61B 18/082* (2013.01); *A61B 18/10* (2013.01); *A61B 34/10* (2016.02); *A61B 34/25* (2016.02); *A61B 90/37* (2016.02); *A61B 5/6853* (2013.01); *A61B 18/02* (2013.01); *A61B 18/18* (2013.01); *A61B 18/20* (2013.01); *A61B 2018/0016* (2013.01); *A61B 2018/0022* (2013.01); *A61B 2018/00267* (2013.01); *A61B 2018/00351* (2013.01); *A61B 2018/00357* (2013.01); *A61B 2018/00577* (2013.01); *A61B 2018/00642* (2013.01); *A61B 2018/00714* (2013.01); *A61B 2018/00791* (2013.01); *A61B 2018/00875* (2013.01); *A61B 2018/0212* (2013.01); *A61B 2018/0237* (2013.01); *A61B 2018/124* (2013.01); *A61B 2018/1407* (2013.01); *A61B 2034/101* (2016.02); *A61B 2562/046* (2013.01)

(58) Field of Classification Search
CPC ................ A61B 5/6858; A61B 5/6869; A61B 2018/0016; A61B 2018/00351; A61B 2018/00375; A61B 2018/00791; A61B 2018/00797; A61B 2018/00815; A61B 2018/00821; A61B 2018/00904
See application file for complete search history.

(56) References Cited

U.S. PATENT DOCUMENTS

| | | |
|---|---|---|
| 4,225,148 A | 9/1980 | Andersson |
| 4,240,441 A | 12/1980 | Khalil |
| 4,263,680 A | 4/1981 | Reul et al. |
| 4,273,128 A | 6/1981 | Lary |
| 4,411,266 A | 10/1983 | Cosman |
| 4,490,859 A | 1/1985 | Black et al. |
| 4,543,090 A | 9/1985 | McCoy |
| 4,699,147 A | 10/1987 | Chilson et al. |
| 4,770,187 A | 9/1988 | Lash et al. |
| 4,787,369 A | 11/1988 | Allred, III et al. |
| 4,794,912 A | 1/1989 | Lia |
| 4,850,957 A | 7/1989 | Summers |
| 4,887,613 A | 12/1989 | Farr et al. |
| 4,890,602 A | 1/1990 | Hake |
| 4,890,612 A | 1/1990 | Kensey |
| 4,893,613 A | 1/1990 | Hake |
| 4,895,166 A | 1/1990 | Farr et al. |
| 4,905,667 A | 3/1990 | Foerster et al. |
| 4,921,499 A | 5/1990 | Hoffman et al. |
| 4,940,064 A | 7/1990 | Desai |
| 4,942,788 A | 7/1990 | Farr et al. |
| 4,979,514 A | 12/1990 | Sekii et al. |
| 4,998,933 A | 3/1991 | Eggers et al. |
| 5,026,384 A | 6/1991 | Farr et al. |
| 5,047,047 A | 9/1991 | Yoon |
| 5,122,137 A | 6/1992 | Lennox |
| 5,127,902 A | 7/1992 | Fischell |
| 5,153,151 A | 10/1992 | Aitken |
| 5,156,151 A | 10/1992 | Imran |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,195,505 A | 3/1993 | Josefsen |
| 5,201,316 A | 4/1993 | Pomeranz et al. |
| 5,228,442 A | 7/1993 | Imran |
| 5,242,386 A | 9/1993 | Holzer |
| 5,245,987 A | 9/1993 | Redmond et al. |
| 5,255,679 A | 10/1993 | Imran |
| 5,279,299 A | 1/1994 | Imran |
| 5,293,869 A | 3/1994 | Edwards et al. |
| 5,297,549 A | 3/1994 | Beatty et al. |
| 5,309,910 A | 5/1994 | Edwards et al. |
| 5,312,435 A | 5/1994 | Nash et al. |
| 5,317,952 A | 6/1994 | Immega |
| 5,324,284 A | 6/1994 | Imran |
| 5,327,889 A | 7/1994 | Imran |
| 5,341,807 A | 8/1994 | Nardella |
| 5,345,936 A | 9/1994 | Pomeranz et al. |
| 5,351,679 A | 10/1994 | Mayzels et al. |
| 5,366,443 A | 11/1994 | Eggers et al. |
| 5,370,679 A | 12/1994 | Atlee, III |
| 5,379,773 A | 1/1995 | Hornsby |
| 5,397,321 A | 3/1995 | Houser et al. |
| 5,419,767 A | 5/1995 | Eggers et al. |
| 5,450,860 A | 9/1995 | O'Connor |
| 5,456,254 A | 10/1995 | Pietroski et al. |
| 5,465,717 A | 11/1995 | Imran et al. |
| 5,478,353 A | 12/1995 | Yoon |
| 5,485,849 A | 1/1996 | Panescu et al. |
| 5,496,267 A | 3/1996 | Drasler et al. |
| 5,499,981 A | 3/1996 | Kordis |
| 5,531,760 A | 7/1996 | Alwafaie |
| 5,545,193 A | 8/1996 | Fleischman et al. |
| 5,549,661 A | 8/1996 | Kordis et al. |
| 5,555,883 A | 9/1996 | Avitall |
| 5,557,967 A | 9/1996 | Renger |
| 5,575,810 A | 11/1996 | Swanson et al. |
| 5,593,424 A | 1/1997 | Northrup, III |
| 5,598,848 A | 2/1997 | Swanson et al. |
| 5,599,345 A | 2/1997 | Edwards et al. |
| 5,620,481 A | 4/1997 | Desai et al. |
| 5,637,090 A | 6/1997 | McGee et al. |
| 5,662,587 A | 9/1997 | Grundfest et al. |
| 5,681,308 A | 10/1997 | Edwards et al. |
| 5,681,336 A | 10/1997 | Clement et al. |
| 5,687,723 A | 11/1997 | Avitall |
| 5,687,737 A | 11/1997 | Branham et al. |
| 5,697,285 A | 12/1997 | Nappi et al. |
| 5,713,896 A | 2/1998 | Nardella |
| 5,713,942 A | 2/1998 | Stern et al. |
| 5,716,397 A | 2/1998 | Myers |
| 5,720,726 A | 2/1998 | Marcadis et al. |
| 5,728,114 A | 3/1998 | Evans et al. |
| 5,730,127 A | 3/1998 | Avitall |
| 5,738,096 A | 4/1998 | Ben-Haim |
| 5,762,066 A | 6/1998 | Law et al. |
| 5,769,846 A | 6/1998 | Edwards et al. |
| 5,782,239 A | 7/1998 | Webster, Jr. |
| 5,782,879 A | 7/1998 | Rosborough et al. |
| 5,800,495 A | 9/1998 | Machek et al. |
| 5,823,189 A | 10/1998 | Kordis |
| 5,824,066 A | 10/1998 | Gross |
| 5,836,947 A | 11/1998 | Fleischman et al. |
| 5,836,990 A | 11/1998 | Li |
| 5,853,422 A | 12/1998 | Huebsch et al. |

(56) References Cited

U.S. PATENT DOCUMENTS

| | | |
|---|---|---|
| 5,868,755 A | 2/1999 | Kanner et al. |
| 5,876,343 A | 3/1999 | Teo |
| 5,881,727 A | 3/1999 | Edwards |
| 5,885,278 A | 3/1999 | Fleischman |
| 5,891,136 A | 4/1999 | McGee et al. |
| 5,893,847 A | 4/1999 | Kordis |
| 5,904,711 A | 5/1999 | Flom et al. |
| 5,916,163 A | 6/1999 | Panescu et al. |
| 5,919,207 A | 7/1999 | Taheri |
| 5,921,924 A | 7/1999 | Avitall |
| 5,935,075 A | 8/1999 | Casscells et al. |
| 5,935,079 A | 8/1999 | Swanson et al. |
| 5,941,251 A | 8/1999 | Panescu et al. |
| 5,944,715 A | 8/1999 | Goble et al. |
| 5,961,440 A | 10/1999 | Schweich, Jr. et al. |
| 5,968,040 A | 10/1999 | Swanson et al. |
| 5,984,950 A | 11/1999 | Cragg et al. |
| 6,001,069 A | 12/1999 | Tachibana et al. |
| 6,001,093 A | 12/1999 | Swanson et al. |
| 6,014,581 A | 1/2000 | Whayne et al. |
| 6,023,638 A | 2/2000 | Swanson |
| 6,030,382 A | 2/2000 | Fleischman et al. |
| 6,036,689 A | 3/2000 | Tu et al. |
| 6,063,082 A | 5/2000 | DeVore et al. |
| 6,071,282 A | 6/2000 | Fleischman |
| 6,104,944 A | 8/2000 | Martinelli |
| 6,106,522 A | 8/2000 | Fleischman et al. |
| 6,119,030 A | 9/2000 | Morency |
| 6,123,702 A | 9/2000 | Swanson et al. |
| 6,138,043 A | 10/2000 | Avitall |
| 6,142,993 A | 11/2000 | Whayne et al. |
| 6,156,046 A | 12/2000 | Passafaro et al. |
| 6,210,432 B1 | 4/2001 | Solem et al. |
| 6,216,043 B1 | 4/2001 | Swanson et al. |
| 6,217,573 B1 | 4/2001 | Webster |
| 6,241,747 B1 | 6/2001 | Ruff |
| 6,248,124 B1 | 6/2001 | Pedros et al. |
| 6,258,258 B1 | 7/2001 | Sartori et al. |
| 6,266,550 B1 | 7/2001 | Selmon et al. |
| 6,304,769 B1 | 10/2001 | Arenson et al. |
| 6,306,135 B1 | 10/2001 | Ellman et al. |
| 6,308,091 B1 | 10/2001 | Avitall |
| 6,319,249 B1 | 11/2001 | Tollner |
| 6,322,559 B1 | 11/2001 | Daulton et al. |
| 6,330,478 B1 | 12/2001 | Lee et al. |
| 6,346,105 B1 | 2/2002 | Tu et al. |
| 6,350,263 B1 | 2/2002 | Wetzig et al. |
| 6,358,258 B1 | 3/2002 | Arcia et al. |
| 6,383,151 B1 | 5/2002 | Diederich et al. |
| 6,389,311 B1 | 5/2002 | Whayne et al. |
| 6,391,024 B1 | 5/2002 | Sun et al. |
| 6,391,048 B1 | 5/2002 | Ginn et al. |
| 6,391,054 B2 | 5/2002 | Carpentier et al. |
| 6,402,781 B1 | 6/2002 | Langberg et al. |
| 6,436,052 B1 | 8/2002 | Nikolic et al. |
| 6,475,223 B1 | 11/2002 | Werp et al. |
| 6,485,409 B1 | 11/2002 | Voloshin et al. |
| 6,485,482 B1 | 11/2002 | Belef |
| 6,485,489 B2 | 11/2002 | Teirstein et al. |
| 6,506,210 B1 | 1/2003 | Kanner |
| 6,514,249 B1 | 2/2003 | Maguire et al. |
| 6,529,756 B1 | 3/2003 | Phan et al. |
| 6,537,198 B1 | 3/2003 | Vidlund et al. |
| 6,537,314 B2 | 3/2003 | Langberg et al. |
| 6,540,670 B1 | 4/2003 | Hirata et al. |
| 6,551,310 B1 | 4/2003 | Ganz et al. |
| 6,551,312 B2 | 4/2003 | Zhang et al. |
| 6,569,160 B1 | 5/2003 | Goldin et al. |
| 6,569,198 B1 | 5/2003 | Wilson et al. |
| 6,575,971 B2 | 6/2003 | Hauck et al. |
| 6,589,208 B2 | 7/2003 | Ewers et al. |
| 6,616,684 B1 | 9/2003 | Vidlund et al. |
| 6,626,930 B1 | 9/2003 | Allen et al. |
| 6,632,238 B2 | 10/2003 | Ginn et al. |
| 6,635,056 B2 | 10/2003 | Kadhiresan et al. |
| 6,640,119 B1 | 10/2003 | Budd et al. |
| 6,662,034 B2 | 12/2003 | Segner et al. |
| D484,979 S | 1/2004 | Fonteine |
| 6,704,590 B2 | 3/2004 | Haldeman |
| 6,723,038 B1 | 4/2004 | Schroeder et al. |
| 6,726,716 B2 | 4/2004 | Marquez |
| 6,760,616 B2 | 7/2004 | Hoey et al. |
| 6,780,197 B2 | 8/2004 | Roe et al. |
| 6,788,969 B2 | 9/2004 | Dupree et al. |
| 6,797,001 B2 | 9/2004 | Mathis et al. |
| 6,800,090 B2 | 10/2004 | Alferness et al. |
| 6,824,562 B2 | 11/2004 | Mathis et al. |
| 6,837,886 B2 | 1/2005 | Collins et al. |
| 6,852,076 B2 | 2/2005 | Nikolic et al. |
| 6,855,143 B2 | 2/2005 | Davison et al. |
| 6,890,353 B2 | 5/2005 | Cohn et al. |
| 6,892,091 B1 | 5/2005 | Ben-Haim et al. |
| 6,899,674 B2 | 5/2005 | Viebach et al. |
| 6,907,297 B2 | 6/2005 | Wellman et al. |
| 6,908,478 B2 | 6/2005 | Alferness et al. |
| 6,913,576 B2 | 7/2005 | Bowman |
| 6,918,903 B2 | 7/2005 | Bass |
| 6,926,669 B1 | 8/2005 | Stewart et al. |
| 6,942,657 B2 | 9/2005 | Sinofsky et al. |
| 6,949,122 B2 | 9/2005 | Adams et al. |
| 6,960,206 B2 | 11/2005 | Keane |
| 6,960,229 B2 | 11/2005 | Mathis et al. |
| 6,986,775 B2 | 1/2006 | Morales et al. |
| 6,989,010 B2 | 1/2006 | Francischelli et al. |
| 6,989,028 B2 | 1/2006 | Lashinski et al. |
| 6,994,093 B2 | 2/2006 | Murphy et al. |
| 6,997,951 B2 | 2/2006 | Solem et al. |
| 7,001,383 B2 | 2/2006 | Keidar |
| 7,025,776 B1 | 4/2006 | Houser et al. |
| 7,048,734 B1 | 5/2006 | Fleischman et al. |
| 7,050,848 B2 | 5/2006 | Hoey et al. |
| 7,052,487 B2 | 5/2006 | Cohn et al. |
| 7,068,867 B2 | 6/2006 | Adoram et al. |
| 7,141,019 B2 | 11/2006 | Pearlman |
| 7,144,363 B2 | 12/2006 | Pai et al. |
| 7,166,127 B2 | 1/2007 | Spence et al. |
| 7,174,201 B2 | 2/2007 | Govari et al. |
| 7,177,677 B2 | 2/2007 | Kaula et al. |
| 7,186,210 B2 | 3/2007 | Feld et al. |
| 7,187,964 B2 | 3/2007 | Khoury |
| 7,189,202 B2 | 3/2007 | Lau et al. |
| 7,198,635 B2 | 4/2007 | Danek et al. |
| 7,255,695 B2 | 8/2007 | Falwell et al. |
| 7,276,044 B2 | 10/2007 | Ferry et al. |
| 7,279,007 B2 | 10/2007 | Nikolic et al. |
| 7,300,435 B2 | 11/2007 | Wham et al. |
| 7,303,526 B2 | 12/2007 | Sharkey et al. |
| 7,335,196 B2 | 2/2008 | Swanson et al. |
| 7,481,808 B2 | 1/2009 | Koyfman et al. |
| 7,507,252 B2 | 3/2009 | Lashinski et al. |
| 7,530,980 B2 | 5/2009 | Hooven |
| 7,660,452 B2 | 2/2010 | Zwirn et al. |
| 7,736,388 B2 | 6/2010 | Goldfarb et al. |
| 7,738,967 B2 | 6/2010 | Salo |
| 8,103,338 B2 | 1/2012 | Harlev et al. |
| D654,588 S | 2/2012 | Taube et al. |
| 8,118,853 B2 | 2/2012 | Grewe |
| 8,150,499 B2 | 4/2012 | Gelbart et al. |
| D660,967 S | 5/2012 | Braido et al. |
| 8,224,432 B2 | 7/2012 | MacAdam et al. |
| D717,954 S | 11/2014 | Hjelle et al. |
| 9,198,713 B2 | 12/2015 | Wallace et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2001/0021867 A1 | 9/2001 | Kordis et al. |
| 2002/0002329 A1 | 1/2002 | Avitall |
| 2002/0016628 A1 | 2/2002 | Langberg et al. |
| 2002/0087156 A1 | 7/2002 | Maguire et al. |
| 2002/0087173 A1 | 7/2002 | Alferness et al. |
| 2002/0099415 A1 | 7/2002 | Panescu et al. |
| 2002/0107478 A1 | 8/2002 | Wendlandt |
| 2002/0107511 A1 | 8/2002 | Collins et al. |

(56) References Cited

U.S. PATENT DOCUMENTS

| | | |
|---|---|---|
| 2002/0107530 A1 | 8/2002 | Saucer et al. |
| 2002/0115941 A1 | 8/2002 | Whayne et al. |
| 2002/0115944 A1 | 8/2002 | Mendes et al. |
| 2002/0169504 A1 | 11/2002 | Alferness et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2003/0028118 A1 | 2/2003 | Dupree et al. |
| 2003/0028183 A1 | 2/2003 | Sanchez et al. |
| 2003/0050685 A1 | 3/2003 | Nikolic et al. |
| 2003/0055420 A1 | 3/2003 | Kadhiresan et al. |
| 2003/0069570 A1 | 4/2003 | Witzel et al. |
| 2003/0069636 A1 | 4/2003 | Solem et al. |
| 2003/0078465 A1 | 4/2003 | Pai et al. |
| 2003/0078671 A1 | 4/2003 | Lesniak et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0176810 A1 | 9/2003 | Maahs et al. |
| 2003/0181819 A1 | 9/2003 | Desai |
| 2003/0229395 A1 | 12/2003 | Cox |
| 2004/0002626 A1 | 1/2004 | Feld et al. |
| 2004/0054279 A1 | 3/2004 | Hanley |
| 2004/0133220 A1 | 7/2004 | Lashinski et al. |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0158321 A1 | 8/2004 | Reuter et al. |
| 2004/0176797 A1 | 9/2004 | Opolski |
| 2004/0181139 A1 | 9/2004 | Falwell et al. |
| 2004/0186566 A1 | 9/2004 | Hindrichs et al. |
| 2004/0215232 A1 | 10/2004 | Belhe et al. |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0065420 A1 | 3/2005 | Collins et al. |
| 2005/0065504 A1 | 3/2005 | Melsky et al. |
| 2005/0080402 A1 | 4/2005 | Santamore et al. |
| 2005/0096047 A1 | 5/2005 | Haberman et al. |
| 2005/0096647 A1 | 5/2005 | Steinke et al. |
| 2005/0107723 A1 | 5/2005 | Wehman et al. |
| 2005/0107871 A1 | 5/2005 | Realyvasquez et al. |
| 2005/0125030 A1 | 6/2005 | Forsberg et al. |
| 2005/0148892 A1 | 7/2005 | Desai |
| 2005/0149014 A1 | 7/2005 | Hauck et al. |
| 2005/0149159 A1 | 7/2005 | Andreas et al. |
| 2005/0154252 A1 | 7/2005 | Sharkey et al. |
| 2005/0182365 A1 | 8/2005 | Hennemann et al. |
| 2005/0187620 A1 | 8/2005 | Pai et al. |
| 2005/0197593 A1 | 9/2005 | Burbank et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203558 A1 | 9/2005 | Maschke |
| 2005/0209636 A1 | 9/2005 | Widomski et al. |
| 2005/0216054 A1 | 9/2005 | Widomski et al. |
| 2005/0240249 A1 | 10/2005 | Tu et al. |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0261580 A1 | 11/2005 | Willis et al. |
| 2005/0267458 A1 | 12/2005 | Paul et al. |
| 2005/0267574 A1 | 12/2005 | Cohn et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |
| 2006/0015038 A1 | 1/2006 | Weymarn-Scharli |
| 2006/0015096 A1 | 1/2006 | Hauck et al. |
| 2006/0025800 A1 | 2/2006 | Suresh |
| 2006/0030881 A1 | 2/2006 | Sharkey et al. |
| 2006/0085049 A1 | 4/2006 | Cory et al. |
| 2006/0089637 A1 | 4/2006 | Werneth et al. |
| 2006/0100618 A1 | 5/2006 | Chan et al. |
| 2006/0106298 A1 | 5/2006 | Ahmed et al. |
| 2006/0135968 A1 | 6/2006 | Schaller |
| 2006/0135970 A1 | 6/2006 | Schaller |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0264980 A1 | 11/2006 | Khairkhahan et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2007/0016068 A1 | 1/2007 | Grunwald et al. |
| 2007/0027533 A1 | 2/2007 | Douk |
| 2007/0038208 A1 | 2/2007 | Kefer |
| 2007/0083193 A1 | 4/2007 | Werneth et al. |
| 2007/0083195 A1 | 4/2007 | Werneth et al. |
| 2007/0088362 A1 | 4/2007 | Bonutti et al. |
| 2007/0115390 A1 | 5/2007 | Makara et al. |
| 2007/0118215 A1 | 5/2007 | Moaddeb |
| 2007/0129717 A1 | 6/2007 | Brown, III et al. |
| 2007/0161846 A1 | 7/2007 | Nikolic et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0232858 A1 | 10/2007 | MacNamara et al. |
| 2007/0249999 A1 | 10/2007 | Sklar et al. |
| 2007/0270688 A1 | 11/2007 | Gelbart et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0045778 A1 | 2/2008 | Lichtenstein et al. |
| 2008/0071298 A1 | 3/2008 | Khairkhahan et al. |
| 2008/0262337 A1 | 10/2008 | Falwell et al. |
| 2008/0281322 A1 | 11/2008 | Sherman et al. |
| 2008/0312713 A1 | 12/2008 | Wilfley et al. |
| 2009/0018617 A1 | 1/2009 | Skelton et al. |
| 2009/0024138 A1 | 1/2009 | Saleh |
| 2009/0069704 A1 | 3/2009 | MacAdam et al. |
| 2009/0131930 A1 | 5/2009 | Gelbart et al. |
| 2009/0157058 A1 | 6/2009 | Ferren et al. |
| 2009/0171274 A1 | 7/2009 | Harlev et al. |
| 2009/0192441 A1 | 7/2009 | Gelbart et al. |
| 2009/0270737 A1 | 10/2009 | Thornton |
| 2009/0287271 A1 | 11/2009 | Blum et al. |
| 2009/0287304 A1 | 11/2009 | Dahlgren et al. |
| 2010/0121147 A1 | 5/2010 | Oskin et al. |
| 2010/0211052 A1 | 8/2010 | Brown et al. |
| 2010/0249771 A1 | 9/2010 | Pearson et al. |
| 2010/0268059 A1 | 10/2010 | Ryu et al. |
| 2011/0125172 A1 | 5/2011 | Gelbart et al. |
| 2011/0172658 A1 | 7/2011 | Gelbart et al. |
| 2011/0213231 A1 | 9/2011 | Hall et al. |
| 2011/0282491 A1 | 11/2011 | Prisco et al. |
| 2012/0158016 A1 | 6/2012 | Gelbart et al. |
| 2012/0165829 A1 | 6/2012 | Chen et al. |
| 2012/0271135 A1 | 10/2012 | Burke et al. |
| 2013/0165916 A1 | 6/2013 | Mathur et al. |
| 2013/0172883 A1 | 7/2013 | Lopes et al. |
| 2013/0178850 A1 | 7/2013 | Lopes et al. |
| 2013/0178851 A1 | 7/2013 | Lopes et al. |
| 2013/0184705 A1 | 7/2013 | Gelbart et al. |
| 2013/0184706 A1 | 7/2013 | Gelbart et al. |
| 2013/0190587 A1 | 7/2013 | Lopes et al. |
| 2013/0190741 A1 | 7/2013 | Moll et al. |
| 2013/0197513 A1 | 8/2013 | Lopes et al. |
| 2013/0241929 A1 | 9/2013 | Massarwa et al. |
| 2013/0304065 A1 | 11/2013 | Lopes et al. |
| 2013/0310828 A1 | 11/2013 | Reinders et al. |
| 2014/0114307 A1 | 4/2014 | Moisa et al. |

(56) References Cited

U.S. PATENT DOCUMENTS

| | | |
|---|---|---|
| 2014/0350552 A1 | 11/2014 | Highsmith |
| 2015/0045660 A1 | 2/2015 | Gelbart et al. |
| 2015/0126993 A1 | 5/2015 | Gelbart et al. |
| 2015/0157400 A1 | 6/2015 | Gelbart et al. |
| 2015/0245798 A1 | 9/2015 | Gelbart et al. |
| 2015/0250539 A1 | 9/2015 | Gelbart et al. |
| 2016/0008062 A1 | 1/2016 | Gelbart et al. |
| 2016/0367315 A1 | 12/2016 | Moisa et al. |
| 2017/0020604 A1 | 1/2017 | Lopes et al. |
| 2017/0035486 A1 | 2/2017 | Lopes et al. |

FOREIGN PATENT DOCUMENTS

| | | |
|---|---|---|
| WO | 9510320 A1 | 4/1995 |
| WO | 95/20349 A1 | 8/1995 |
| WO | 97/17892 A1 | 5/1997 |
| WO | 0108575 A2 | 2/2001 |
| WO | 02087437 A1 | 11/2002 |
| WO | 03015611 A2 | 2/2003 |
| WO | 03077800 A1 | 9/2003 |
| WO | 2004012629 A1 | 2/2004 |
| WO | 2004047679 A1 | 6/2004 |
| WO | 2004084746 A2 | 10/2004 |
| WO | 2004100803 A1 | 11/2004 |
| WO | 2005070330 A1 | 8/2005 |
| WO | 2005102181 A1 | 11/2005 |
| WO | 2006017809 A2 | 2/2006 |
| WO | 2006105121 A2 | 10/2006 |
| WO | 2006135747 A2 | 12/2006 |
| WO | 2006135749 A2 | 12/2006 |
| WO | 2007021647 A2 | 2/2007 |
| WO | 2007115390 A1 | 10/2007 |
| WO | 2008002606 A2 | 1/2008 |
| WO | 2009011721 A1 | 1/2009 |
| WO | 2009065042 A2 | 5/2009 |
| WO | 2012050877 A1 | 4/2012 |
| WO | 2012/100184 A2 | 7/2012 |
| WO | 2012/100185 A2 | 7/2012 |
| WO | 2013/173917 A1 | 11/2013 |

OTHER PUBLICATIONS

Non-Final Office Action issued in U.S. Appl. No. 14/229,305 dated Apr. 29, 2016.
Notice of Allowance issued in U.S. Appl. No. 13/793,076 dated Jul. 7, 2016.
Notice of Allowance issued in U.S. Appl. No. 13/793,213 dated Aug. 10, 2016.
Non-Final Office Action issued in U.S. Appl. No. 13/942,354 dated Aug. 4, 2016.
Notice of Allowance issued in U.S. Appl. No. 14/136,946 dated May 12, 2016.
Notice of Allowance issued in U.S. Appl. No. 13/782,867 dated Aug. 12, 2016.
Notice of Allowance issued in U.S. Appl. No. 3/782,903 dated Jul. 6, 2016.
Corrected Notice of Allowance issued in U.S. Appl. No. 13/782,903 dated Jul. 19, 2016.
Office Action issued in U.S. Appl. No. 14/564,463 dated Feb. 28, 2017.
Notice of Allowance issued in U.S. Appl. No. 13/942,354 dated Feb. 10, 2017.
Lopes et al., "Enhanced Medical Device for Use in Bodily Cavities, for Example an Atrium", Amendment filed Aug. 24, 2015 for U.S. Appl. No. 13/782,889, 21 pages.
Lopes et al., "Enhanced Medical Device for Use in Bodily Cavities, for Example an Atrium", Amendment filed Aug. 28, 2015 for U.S. Appl. No. 13/782,903, 19 pages.
Lopes et al., "Enhanced Medical Device for Use in Bodily Cavities, for Example an Atrium", Amendment filed Sep. 14, 2015 for U.S. Appl. No. 13/782,867, 25 pages.
Lopes et al., "High-Density Electrode-Based Medical Device System", Amendment filed Oct. 9, 2015 for U.S. Appl. No. 13/793,213, 26 pages.
Lopes et al., "High-Density Electrode-Based Medical Device System", Amendment filed Oct. 9, 2015 for U.S. Appl. No. 13/793,076, 14 pages.
Examination Report issued in EP13172848.7, dated Sep. 21, 2015.
Office Action issued in U.S. Appl. No. 13/785,910, dated Nov. 2, 2016.
Notice of Allowance issued in U.S. Appl. No. 14/229,305, dated Nov. 8, 2016.
Notice of Allowance issued in U.S. Appl. No. 14/229,250, dated Dec. 7, 2016.
Notice of Allowance issued in U.S. Appl. No. 13/793,076, dated Feb. 10, 2016.
Non-Final Office Action issued in U.S. Appl. No. 13/785,910 dated Apr. 8, 2016.
Bard, "Mesh Ablator Catheter", Brochure, 2008, 4 pgs, Bard Electrophysiology Division, C.R. Bard Inc., 55 Technology Drive Lowell, MA 07851 USA.
Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
"Constellation Mapping Catheters", Brochure, Boston Scientific Corp., 2 pgs © 2007 Boston Scientific Corporation.
"Waveforms and Segments", Ensite System Instructions for use, 54-06154-001 Rev02, Chapter 7 pp. 85-90 © 2007 St. Jude Medical.
Extended European Search Report and EP search opinion for EP 12736677.1, dated Mar. 28, 2014, corresponding to PCT/US2012/022061.
Extended European Search Report and EP search opinion for EP 12736962.7, dated Mar. 28, 2014, corresponding to PCT/US2012/022062.
Extended European Search Report dated Aug. 20, 2013 issued in EP Patent Application No. 13172848.7.
Written Opinion dated Aug. 22, 2012 for PCT/US2012/022061, 6 pgs.
International Search Report and Written Opinion dated Aug. 2, 2013 issued in PCT/CA2013/050350.
International Search Report and Written Opinion dated Sep. 17, 2013 issued in PCT/US2013/039982.
International Search Report and Written Opinion dated Sep. 27, 2013 issued in PCT/US2013/039977.
International Search Report dated Jul. 30, 2012 for PCT/US2012/022062, 5 pgs.
Written Opinion dated Jul. 30, 2012 for PCT/US2012/022062, 5 pgs.
International Search Report dated Aug. 22, 2012 for PCT/US2012/022061, 5 pgs.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs , Biosense Webster, Inc. 3333 Diamond Canyon Road Diamond Bar, CA 91765, USA, © Biosense Webster, Inc. 2009 All rights reserved. 1109003.0.
Gelbart "Medical Device for Use in Bodily Lumens, for Example an Atrium", OA dated Jul. 25, 2011 for U.S. Appl. No. 11/941,819, now published as US 2009-0131930 A1.
Gelbart et al, "Apparatus and Method for Intra-Cardiac Mapping and Ablation", Notice of Allowance dated Oct. 23, 2014 for U.S. Appl. No. 11/475,950, 10 pgs.
Gelbart et al., "Medical Device for Use in Bodily Lumens, for Example an Atrium", Notice of Allowance dated Nov. 13, 2014 for U.S. Appl. No. 13/070,215, 54 pages.
International Search Report dated Mar. 10, 2015, for International Application PCT/CA2014/051144; 10 pages.
Written Opinion dated Mar. 10, 2015, for International Application PCT/CA2014/051144; 4 pages.
Official Action issued in CN201280004400.9, dated Dec. 3, 2014.
Non-final Office Action issued in U.S. Appl. No. 13/782,867, dated Apr. 15, 2015.

(56) References Cited

OTHER PUBLICATIONS

Non-final Office Action issued in U.S. Appl. No. 13/782,903, dated Apr. 28, 2015.
Non-final Office Action issued in U.S. Appl. No. 13/782,889, dated May 22, 2015.
Non-final Office Action issued in U.S. Appl. No. 13/793,076, dated Jul. 10, 2015.
Non-final Office Action issued in U.S. Appl. No. 13/793,213, dated Jul. 9, 2015.
Gelbart et al, "Apparatus and Method for Intra-Cardiac Mapping and Ablation", Preliminary Amendment filed Aug. 22, 2014; Preliminary Remarks filed Mar. 5, 2013 for U.S. Appl. No. 13/785,931, 10 pgs.
Gelbart et al., "Apparatus and Method for Intra-Cardiac Mapping and Ablation", Office Action dated Aug. 5, 2015 for U.S. Appl. No. 13/785,910, 79 pages.
Gelbart et al., "Apparatus and Method for Intra-Cardiac Mapping and Ablation", Amendment filed in co-pending U.S. Appl. No. 13/785,910 dated Mar. 24, 2017, 30 pgs.
Gelbart et al., "Medical Device for Use in Bodily Lumens, for Example an Atrium", Amendment filed in co-ending U.S. Appl. No. 14/521,692 dated Mar. 31, 2017, 9 pgs.
Office Action issued in Chinese Patent Application No. 201510432392.3 dated Mar. 8, 2017. English concise Explanation of Relevance provided.
Notice of Allowance issued in copending U.S. Appl. No. 14/521,692 dated May 19, 2017.
Office Action issued in copending U.S. Appl. No. 14/713,114 dated Jun. 1, 2017.
Quayle Action issued in copending U.S. Appl. No. 14/713,190 dated May 30, 2017.
Office Action issued in German Application No. 112008003108.8 dated May 8, 2017. English translation provided.
Amendment filed in copending U.S. Appl. No. 14/564,463, filed May 25, 2017.
European Search Report issued in European Patent Application No. 14871405.8 dated Jul. 5, 2017.
Office Action issued in copending U.S. Appl. No. 14/564,463 dated Jul. 17, 2017.
Response to Quayle Action filed in copending U.S. Appl. No. 14/713,190 dated Jul. 24, 2017.
Preliminary Amendment filed in copending U.S. Appl. No. 14/521,692 dated Oct. 23, 2014.
Copending U.S. Appl. No. 15/663,077, filed Jul. 28, 2017.
Preliminary Amendment filed in copending U.S. Appl. No. 15/663,077 dated Aug. 8, 2017.
Extended European Search Report issued in EP13793216.6, dated Oct. 30, 2015.
Extended European Search Report issued in EP15188407.9, dated Jan. 21, 2016.
Lopes et al. "Enhanced Medical Device for Use in Bodily Cavities, for Example an Atrium", Office Action dated Jan. 25, 2016 for U.S. Appl. No. 13/782,867, 49 pages.
Summons to Attend Oral Proceedings issued in European Appln. No. 13172848.7, dated Sep. 1, 2016.
Notice of Allowance issued in U.S. Appl. No. 29/509,636, dated Sep. 27, 2016.
Notice of Allowance issued in U.S. Appl. No. 29/509,621, dated Sep. 27, 2016.
Notice of Allowance issued in U.S. Appl. No. 13/782,889, dated Aug. 25, 2016.
Lopes et al., "Intra-Cardiac Procedure Device", Amendment filed in co-pending U.S. Appl. No. 29/509,636, filed Jul. 22, 2016, 5 pgs.
Lopes et al., "Intra-Cardiac Procedure Device", Amendment filed in co-pending U.S. Appl. No. 29/509,636 dated Nov. 17, 2016, 3 pgs.
Lopes et al., "High-Density Electrode-Based Medical Device System", Preliminary Amendment filed in co-pending U.S. Appl. No. 15/287,988 dated Nov. 23, 2016, 9 pgs.
Lopes et al., "Intra-Cardiac Procedure Device", Amendment filed in co-pending U.S. Appl. No. 29/509,621 dated Jul. 22, 2016, 5 pgs.
Lopes et al., "Intra-Cardiac Procedure Device", Amendment filed in co-pending U.S. Appl. No. 29/509,621 dated Nov. 17, 2016, 3 pgs.
Lopes et al., "High-Density Electrode-Based Medical Device System" Amendment filed in co-pending U.S. Appl. No. 13/793,213 dated May 26, 2016, 39 pgs.
Lopes et al., "Enhanced Medical Device for Use in Bodily Cavities, for Example an Atrium", Preliminary Amendment filed in co-pending U.S. Appl. No. 15/299,640 dated Oct. 21, 2016, 4 pgs.
Lopes et al., "Enhanced Medical Device for Use in Bodily Cavities, for Example an Atrium", Preliminary Amendment filed in co-pending U.S. Appl. No. 15/299,640 dated Dec. 9, 2016, 11 pgs.
Gelbart et al., "Intra-Cardiac Mapping and Ablation Method", Amendment filed in co-pending U.S. Appl. No. 11/475,950 dated Feb. 12, 2013, 4 pgs.
Moisa et al., "Catheter System", Preliminary Amendment filed in co-pending U.S. Appl. No. 15/254,130 dated Sep. 19, 2016, 22 pgs.
Gelbart et al., "Apparatus and Method for Intra-Cardiac Mapping and Ablation", Preliminary Amendment filed in co-pending U.S. Appl. No. 14/804,810 dated Jul. 30, 2015, 10 pgs.
Lopes et al., "Enhanced Medical Device for Use in Bodily Cavities, for Example an Atrium", Amendment filed in co-pending U.S. Appl. No. 13/782,867 dated May 17, 2016, 39 pgs.
Gelbart et al., "Medical Device for Use in Bodily Lumens, for Example an Atrium", Preliminary Amendment filed in co-pending U.S. Appl. No. 14/713,190 dated May 15, 2015, 3 pgs.
Gelbart et al., "Medical Device for Use in Bodily Lumens, for Example an Atrium", Preliminary Amendment filed in co-pending U.S. Appl. No. 14/713,190 dated Jun. 16, 2015, 7 pgs.
Gelbart et al., "Medical Device for Use in Bodily Lumens, for Example an Atrium", Preliminary Amendment filed in co-pending U.S. Appl. No. 14/713,114 dated Jun. 16, 2015, 8 pgs.
Office Action issued in co-pending U.S. Appl. No. 14/521,692 dated Jan. 10, 2017.
Gelbart et al., "Medical Device for Use in Bodily Lumens, for Example an Atrium", Amendment filed in co-pending U.S. Appl. No. 14/229,305 dated Sep. 27, 2016, 15 pgs.
Lopes et al., "Enhanced Medical Device for Use in Bodily Cavities, for Example an Atrium", Amendment filed in co-pending U.S. Appl. No. 13/782,889 dated May 17, 2016, 51 pgs.
Gelbart et al., "Medical Device for Use in Bodily Lumens, for Example an Atrium", Amendment filed in co-pending U.S. Appl. No. 14/229,250 dated Sep. 27, 2016, 13 pgs.
Gelbart et al., "Apparatus and Method for Intra-Cardiac Mapping and Ablation", Amendment filed in co-pending U.S. Appl. No. 13/785,910 dated Aug. 8, 2016, 18 pgs.
Moisa et al., "Catheter System", Amendment filed in co-pending U.S. Appl. No. 14/136,946 dated Apr. 18, 2016, 19 pgs.
Lopes et al., "Enhanced Medical Device for Use in Bodily Cavities, for Example an Atrium", Amendment filed in co-pending U.S. Appl. No. 13/942,354 dated Jan. 4, 2017, 23 pgs.
Lopes et al., "High-Density Electrode-Based Medical Device System", Preliminary Amendment filed in co-pending-pending U.S. Appl. No. 13/793,076 dated May 26, 2016, 15 pgs.
Lopes et al., "High-Density Electrode-Based Medical Device System", Amendment filed in co-pending U.S. Appl. No. 13/793,076 dated May 9, 2016, 15 pgs.
Gelbart et al., "Apparatus and Method for Intracardiac Mapping and Ablation", Preliminary Amendment filed in co-pending U.S. Appl. No. 13/785,931 dated Mar. 5, 2013, 2 pgs.
Gelbart et al., "Apparatus and Method for Intra-Cardiac Mapping and Ablation", Amendment filed in co-pending U.S. Appl. No. 13/785,910 dated Feb. 9, 2016, 11 pgs.
Gelbart et al., "Apparatus and Method for Intra-Cardiac Mapping and Ablation", Amendment filed in co-pending U.S. Appl. No. 13/785,910 dated Jan. 5, 2016, 15 pgs.
Decision to Refuse a European Patent Application issued in European Patent Application No. 13172848.7 dated Feb. 22, 2017.
Moisa et al., "Catheter System ", Office Action dated Nov. 16, 2015 for U.S. Appl. No. 14/136,946, 92 pages.
Office Action issued in U.S. Appl. No. 13/782,889, dated Dec. 18, 2015.
Office Action issued in U.S. Appl. No. 13/782,903, dated Dec. 18, 2015.

(56) References Cited

OTHER PUBLICATIONS

Final Office Action issued in U.S. Appl. No. 13/793,213, dated Feb. 26, 2016.
Non-Final Office Action issued in U.S. Appl. No. 29/509,719, dated Feb. 25, 2016.
Quayle issued in U.S. Appl. No. 29/509,621, dated Feb. 26, 2016.
Quayle issued in U.S. Appl. No. 29/509,636, dated Feb. 26, 2016.
Amendment filed in copending U.S. Appl. No. 14/713,114, filed Aug. 23, 2017.
Notice of Allowance issued in copending U.S. Appl. No. 14/713,190 dated Aug. 28, 2017.
Office Action issued in copending U.S. Appl. No. 13/785,910 dated Aug. 30, 2017.
Buchbinder,Maurice MD, "Dynamic Mitral Valve Annuloplasty: A Reshapable Ring for Residual and Recurring MR," from the Foundation for Cardiovascular Medicine, La Jolla, CA. May 24, 2007.
Gabriel et al., "The Dielectric Properties of Biological Tissues: I. Literature Survey," Phys. Med. Biol. 41:2231-2249, 1996.
Konings et al., "Development of an Intravascular Impedance Catheter for Detection of Fatty Lesions in Arteries," IEEE Transactions on Medical Imaging, 16(4):439-446, 1997.
Mack, "New Techniques for Percutaneous Repair of the Mitral Valve," Heart Failure Review, 11:259-268, 2006.
Otasevic et al., "First-in-Man Implantation of Left Ventricular Partitioning Device in a Patient With Chronic Heart Failure: Twelve-Month Follow-up," Journal of Cardiac Failure 13(7):517-520, 2007.
Sharkey et al., "Left Ventricular Apex Occluder. Description of a Ventricular Partitioning Device," EuroIntervention 2:125-127, 2006.
Stiles, et al., "Simulated Characterization of Atherosclerotic Lesions in the Coronary Arteries by Measurement of Bioimpedance," IEE Transactions on Biomedical Engineering, 50(7):916-921,2003.
Tanaka et al., "Artificial SMA Valve for Treatment of Urinary Incontinence: Upgrading of Valve and Introduction of Transcutaneous Transformer," Bio-Medical Materials and Engineering 9:97-112, 1999.
Timek et al.., "Septal-Lateral Annular Cinching ('SLAC') Reduces Mitral Annular Size Without Perturbing Normal Annular Dynamics," Journal of Heart Valve Disease 11 (1):2-10, 2002.
Timek et al., "Septal-Lateral Annular Cinching Abolishes Acute Ischemic Mitral Regurgitation," Journal of Thoracic and Cardiovascular Surgery, 123(5):881-888, 2002.
Valvano et al., "Thermal Conductivity and Diffusivity of Biomaterials Measured with Self-Heated Thermistors," International Journal of Thermodynamics, 6(3):301-311, 1985.
Gelbart et al., "Automatic Atherectomy System," Office Action dated Mar. 4, 2009 for U.S. Appl. No. 11/436,584, 7 pages.
Gelbart et al., "Automatic Atherectomy System," Amendment filed Aug. 4, 2009 for U.S. Appl. No. 11/436,584, 35 pages.
Gelbart et al., "Automatic Atherectomy System," Office Action dated Dec. 1, 2009 for U.S. Appl. No. 11/436,584, 10 pages.
Gelbart et al., "Automatic Atherectomy System," Amendment filed Mar. 30, 2010 for U.S. Appl. No. 11/436,584, 20 pages.
Gelbart et al., "Automatic Atherectomy System," Amendment filed Oct. 25, 2010 for U.S. Appl. No. 11/436,584, 9 pages.
Gelbart et al., "Automatic Atherectomy System," Office Action dated Dec. 14, 2010 for U.S. Appl. No. 11/436,584, 12 pages.
Gelbart et al., "Intra-Cardiac Mapping and Ablation Method," Preliminary Amendment filed Aug. 29, 2007 for U.S. Appl. No. 11/475,950,42 pages.
Gelbart et al., "Intra-Cardiac Mapping and Ablation Method," Amendment filed Mar. 5, 2008 for U.S. Appl. No. 11/475,950, 11 pages.
Gelbart et al., "Intra-Cardiac Mapping and Ablation Method," Office Action dated Jun. 23, 2010 for U.S. Appl. No. 11/475,950, 18 pages.
Gelbart et al., "Intra-Cardiac Mapping and Ablation Method," Amendment filed Aug. 16, 2010 for U.S. Appl. No. 11/475,950, 22 pages.
Gelbart et al., "Intra-Cardiac Mapping and Ablation Method," Office Action dated Nov. 23, 2010 for U.S. Appl. No. 11/475,950, 25 pages.
Gelbart et al., "Intra-Cardiac Mapping and Ablation Method," Amendment filed Feb. 23, 2011 for U.S. Appl. No. 11/475,950, 28 pages.
Gelbart et al., "Automatic Atherectomy System," Office Action dated Jun. 15, 2011, for U.S. Appl. No. 12/950,871, 16 pages.
Gelbart et al., "Liposuction System," Office Action dated Mar. 16, 2011 for U.S. Appl. No. 12/010,458, 12 pages.
Gelbart et al., "Liposuction System," Amendment filed Jun. 10, 2011 for U.S. Appl. No. 12/010,458, 10 pages.
Lichtenstein "Method and Apparatus for Percutaneous Reduction of Anterior-Posterior Diameter of Mitral Valve," U.S. Appl. No. 10/690,131, filed Oct. 20, 2003, 31 pages.
International Search Report, dated Dec. 5, 2007, for PCT/US2007/014902, 5 pages.
International Preliminary Report on Patentability, issued Jan. 6, 2009, for PCT/US2007/014902, 8 pages.
International Search Report, dated Dec. 2, 2009, for PCT/US2008/083644, 5 pages.
Written Opinion, dated Dec. 5, 2007, for PCT/US2007/014902, 7 pages.
Written Opinion, dated Dec. 2, 2009, for PCT/US2008/083644, 9 pages.
Gelbart et al., "Automatic Atherectomy System," Amendment filed Sep. 15, 2011 for U.S. Appl. No. 12/950,871, 21 pages.
Gelbart et al., "Liposuction System," Amendment filed Dec. 7, 2011 for U.S. Appl. No. 12/010,458, 15 pages.
Gelbart et al., "Liposuction System," Office Action dated Sep. 14, 2011 for U.S. Appl. No. 12/010,458, 9 pages.
Becker R. et al, "Ablation of Atrial Fibrillation: Energy Sources and Navigation Tools: A Review", Journal of Electrocardiology, 37 (Supplement 2004): 55-62, 2004.
Calkins, Hugh, "Radiofrequency Catheter Ablation of Supraventricular Arrhythmias", Heart, 85:594-600, 2001.
De Ponti et al., "Non-Fluoroscopic Mapping Systems for Electrophysiology: The 'Tool or Toy' Dilemma After 10 Years",European Heart Journal 27:1134-1136, 2006.
Gelbart et al, "Apparatus and Method for Intra-Cardiac Mapping and Ablation", Office Action dated Dec. 13, 2013; Notice of Allowance dated Jul. 25, 2014 for U.S. Appl. No. 11/475,950, 19 pgs.
Gelbart et al., "Medical Device for Use in Bodily Lumens, for Example an Atrium", Office Action dated Jan. 3, 2012; Office Action dated Apr. 3, 2014; Notice of Allowance dated Aug. 26, 2014 for U.S. Appl. No. 11/941,819, 35 pgs.
Gelbart et al, "Apparatus and Method for Intra-Cardiac Mapping and Ablation", Amendment filed Apr. 10, 2014; Supplemental Amendment filed Feb. 12, 2013 for U.S. Appl. No. 11/475,950, 21 pgs.
Gelbart et al, "Apparatus and Method for Intra-Cardiac Mapping and Ablation", Preliminary Amendment filed Aug. 22, 2014; Preliminary Amendment filed Mar. 5, 2013 for U.S. Appl. No. 13/785,910, 10 pgs.
Gelbart et al, "Apparatus and Method for Intra-Cardiac Mapping and Ablation", Preliminary Amendment filed Aug. 22, 2014; Preliminary Amendment filed Mar. 5, 2013 for U.S. Appl. No. 13/785,931, 10 pgs.
Lopes et al, "Enhanced Medical Device for Use in Bodily Cavities, for Example an Atrium", Preliminary Amendment filed Oct. 22, 2013 for U.S. Appl. No. 13/942,354, 13 pgs.
Lopes et al, "Enhanced Medical Device for Use in Bodily Cavities, for Example an Atrium", Preliminary Amendment filed Aug. 20, 2014 for U.S. Appl. No. 13/782,889, 11 pgs.
Lopes et al, "Enhanced Medical Device for Use in Bodily Cavities, for Example an Atrium", Preliminary Amendment filed Mar. 14, 2013 for U.S. Appl. No. 13/782,867, 8 pgs.
Gelbart et al., "Medical Device for Use in Bodily Lumens, for Example an Atrium", Amendment filed Jul. 3, 2014; Amendment filed Apr. 2, 2012; Amendment filed Mar. 1, 2012; Amendment filed Nov. 23, 2011; Replacement drawings filed Feb. 13, 2008 for U.S. Appl. No. 11/941,819, 78 pgs.

(56) References Cited

OTHER PUBLICATIONS

Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,305, 12 pgs.

Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,250, 10 pgs.

Gelbart et al., Medical Device for Use in Bodily Lumens, for Example an Atrium, Amendment filed Sep. 22, 2014, for U.S. Appl. No. 13/070,215, 18 pgs.

Gelbart et al., Medical Device for Use in Bodily Lumens, for Example an Atrium, Office Action dated Jun. 20, 2014, for U.S. Appl. No. 13/070,215, 8 pgs.

Gelbart et al., "Medical Device for Use in Bodily Lumens, for Example an Atrium", Supplemental Notice of Allowance dated Oct. 6, 2014 for U.S. Appl. No. 11/941,819, 4 pgs.

Copending U.S. Appl. No. 15/697,744, filed Sep. 7, 2017.

Copending U.S. Appl. No. 15/725,731, filed Oct. 5, 2017.

Copending U.S. Appl. No. 15/725,662, filed Oct. 5, 2017.

Preliminary Amendment filed in copending U.S. Appl. No. 15/697,744 dated Sep. 21, 2017.

Copending U.S. Appl. No. 15/784,555, filed Oct. 16, 2017.

Copending U.S. Appl. No. 15/784,647, filed Oct. 16, 2017.

Copending U.S. Appl. No. 15/784,722, filed Oct. 16, 2017.

Copending U.S. Appl. No. 15/784,775, filed Oct. 16, 2017.

Amendment filed in copending U.S. Appl. No. 14/564,463 dated Oct. 17, 2017.

Notice of Allowance issued in copending U.S. Appl. No. 14/713,114 dated Nov. 1, 2017.

Notice of Allowance issued in copending U.S. Appl. No. 14/564,463 dated Nov. 9, 2017.

Preliminary Amendment filed in copending U.S. Appl. No. 15/784,555 dated Nov. 7, 2017.

Preliminary Amendment filed in copending U.S. Appl. No. 15/784,775 dated Nov. 7, 2017.

Preliminary Amendment filed in copending U.S. Appl. No. 15/784,722 dated Nov. 7, 2017.

Preliminary Amendment filed in copending U.S. Appl. No. 15/725,731 dated Oct. 24, 2017.

Preliminary Amendment filed in copending U.S. Appl. No. 15/784,647 dated Nov. 7, 2017.

Preliminary Amendment filed in copending U.S. Appl. No. 15/725,662 dated Oct. 24, 2017.

Response to Office Action filed in copending U.S. Appl. No. 13/785,910 dated Nov. 30, 2017.

Amendment filed in copending U.S. Appl. No. 13/785,910 dated Feb. 27, 2018.

Examination Report issued in European Application No. 13793216.6 dated Nov. 24, 2017.

Office Action issued in Chinese Application No. 201510432392.3 dated Nov. 17, 2017. English translation provided.

Examination Report issued in European Application No. 15188407.9 dated Dec. 11, 2017.

Office Action issued in copending U.S. Appl. No. 13/785,910 dated Jan. 12, 2018.

Amendment filed in copending U.S. Appl. No. 14/804,810 dated Feb. 27, 2018.

Office Action issued in copending U.S. Appl. No. 14/804,810 dated Nov. 30, 2017.

APPARATUS AND METHOD FOR INTRA-CARDIAC MAPPING AND ABLATION

CROSS-REFERENCE TO RELATED APPLICATIONS

This application is a continuation of prior U.S. patent application Ser. No. 13/785,931, filed Mar. 5, 2013, now U.S. Pat. No. 9,119,633, issued on Sep. 1, 2015, which is a continuation-in-part of prior U.S. patent application Ser. No. 11/475,950, filed Jun. 28, 2006, now U.S. Pat. No. 8,920,411, issued on Dec. 30, 2014, the entire disclosure of each of these applications is hereby incorporated herein by reference.

TECHNICAL FIELD

This disclosure generally relates to minimally invasive heart surgery, also known as percutaneous cardiac surgery and particularly relates to percutaneous mapping and ablation.

BACKGROUND

Atrial fibrillation is a well known disorder in which spurious electrical signals cause an irregular heart beat. The disorder has a well known cure known as the Maze procedure, in which a border is ablated around the sources of the spurious signals, typically in the left atrium but sometimes in the right atrium. The procedure is very commonly performed under direct vision, but difficult to perform percutaneously via a catheter because of the associated risk. Any error in navigation inside the heart can cause fatal damage. The key to a percutaneous procedure is mapping of the inside of the right and left atrium. Access to the right atrium is simple via the superior vena cava; the left atrium can be reached i) by perforating the transatrial septum, ii) via the aorta and the left ventricle or iii) via the pulmonary veins.

Prior approaches to map the inside of the atrium relied on electrical activity picked up from the atrium wall. These approaches require intimate electrical contact, not always possible because of scar tissue and deposits. These approaches may fail to accurately map the edges of the openings where the veins enter the atrium; information that is useful for correct placement of the ablation pattern. Other mapping methods, such as using an array of ultrasonic transducers, are not practical since such arrays typically will not fit through a catheter of a reasonable size (8-10 mm diameter). A superior mapping apparatus and method, that enables safe execution of the Maze and other intra-cardiac procedures is desirable.

A good survey article on the subject is: "Ablation of Atrial Fibrillation: Energy Sources and Navigation Tools: A survey" by Ruediger Becker and Wolfgang Schoels (J. of Electrocardiology, Vol 37, 2004, pp 55-61). The article includes an extensive bibliography.

SUMMARY

Embodiments of an intra-cardiac mapping system are based on locating openings or ports and values through which blood flows in or out of the heart chambers. For many procedures, such as ablation to cure atrial fibrillation, accurately locating the pulmonary veins and the mitral valve allows performance of a Maze procedure. The openings, ports and valves may be located based on the convective cooling effect of the blood flow. The mapping can be performed by a catheter-deployed expandable net or a scanning catheter. The same net or catheter can also perform the ablation procedure.

In one embodiment, a method for intra-cardiac mapping comprises: introducing a plurality of flow sensors into an intra-cardiac cavity: locating points in a wall forming said cavity based on sensing blood flow; and mapping said walls of said cavity based on said points. The method for intra-cardiac mapping may include said blood flow being sensed by its convective cooling effect on a heated sensor. The method for intra-cardiac mapping may include said sensing being done by a steerable linear array. The method for intra-cardiac mapping may include said mapping being used for treating atrial fibrillation by RF ablation. The method for intra-cardiac mapping may include being used for treating atrial fibrillation by microwave ablation. The method for intra-cardiac mapping may include said mapping being used for treating atrial fibrillation by cryogenic ablation. The method for intra-cardiac mapping may include said mapping being used for treating atrial fibrillation by laser ablation. The method for intra-cardiac mapping may include said blood flow being sensed by the resistance change of a heated resistive wire.

In another embodiment, a method for intra-cardiac mapping comprises: introducing an expandable sensing mesh into said cavity via a catheter; using said mesh to locate openings in walls forming said cavity based on the convective heat transfer of blood flowing through said holes; and mapping inside of said cavity based on location of said openings. The method for intra-cardiac mapping may include said blood flow being sensed by its convective cooling effect on a heated sensor. The method for intra-cardiac mapping may include said sensing being done by a steerable linear array. The method for intra-cardiac mapping may include said mapping being used for treating atrial fibrillation by RF ablation. The method for intra-cardiac mapping may include said mapping being used for treating atrial fibrillation by microwave ablation. The method for intra-cardiac mapping may include said mapping being used for treating atrial fibrillation by cryogenic ablation. The method for intra-cardiac mapping may include said mapping being used for treating atrial fibrillation by laser ablation. The method for intra-cardiac mapping may include said blood flow being sensed by the resistance change of a heated resistive wire. The method for intra-cardiac mapping may include said mesh comprising small coils of nickel wire wound on a mesh of a flexible insulator. The method for intra-cardiac mapping may include an electronic switch used to minimize the number of electrical wires passing through said catheter.

In yet another embodiment, a method for treating atrial fibrillation comprises: introducing at least one flow sensor into an intra-cardiac cavity; locating points in a wall forming said cavity based on sensing blood flow; mapping walls of said cavity based on said points; and ablating a pattern into walls of said cavity based on said mapping. The method for treating atrial fibrillation may include said blood flow being sensed by its convective cooling effect on a heated sensor. The method for treating atrial fibrillation may include said sensing being done by a steerable linear array. The method for treating atrial fibrillation may include said mapping being used for treating atrial fibrillation by RF ablation. The method for treating atrial fibrillation may include said mapping being used for treating atrial fibrillation by microwave ablation. The method for treating atrial fibrillation may include said mapping being used for treating atrial fibrillation by cryogenic ablation. The method for treating atrial fibrillation may include said mapping being used for treating atrial fibrillation by laser ablation. The method for treating atrial fibrillation may include said blood flow being sensed by the resistance change of a heated resistive wire. The method for treating atrial fibrillation may include said flow sensors also acting as electrodes for said ablation. The method for treating atrial fibrillation may include said flow sensor being based on temperature sensing and a same sensor being used to monitor temperature during said ablation. The method for treating atrial fibrillation may include said ablation being unipolar. The method for treating atrial fibrillation may include said ablation being bipolar. The method for treating atrial fibrillation may include said ablated pattern being a Maze procedure.

BRIEF DESCRIPTION OF THE DRAWINGS

In the drawings, identical reference numbers identify similar elements or acts. It is to be understood that the attached drawings are for purposes of illustrating the concepts of the invention and may not be to scale. For example, the sizes, relative positions, shapes, and angles of or associated with elements in the drawings are not necessarily drawn to scale, and some elements may be arbitrarily enlarged and positioned to improve drawing legibility. Further, the particular shapes of the elements as drawn may differ from their actual shapes and, in this regard, may be selected instead of the respective actual shapes for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with apparatuses and methods for intra-cardiac mapping and ablation have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its non-exclusive sense including "and/or" unless the content clearly dictates otherwise.

The headings and Abstract of the Disclosure provided herein are for convenience only and do not interpret the scope or meaning of the embodiments.

Figure 1:
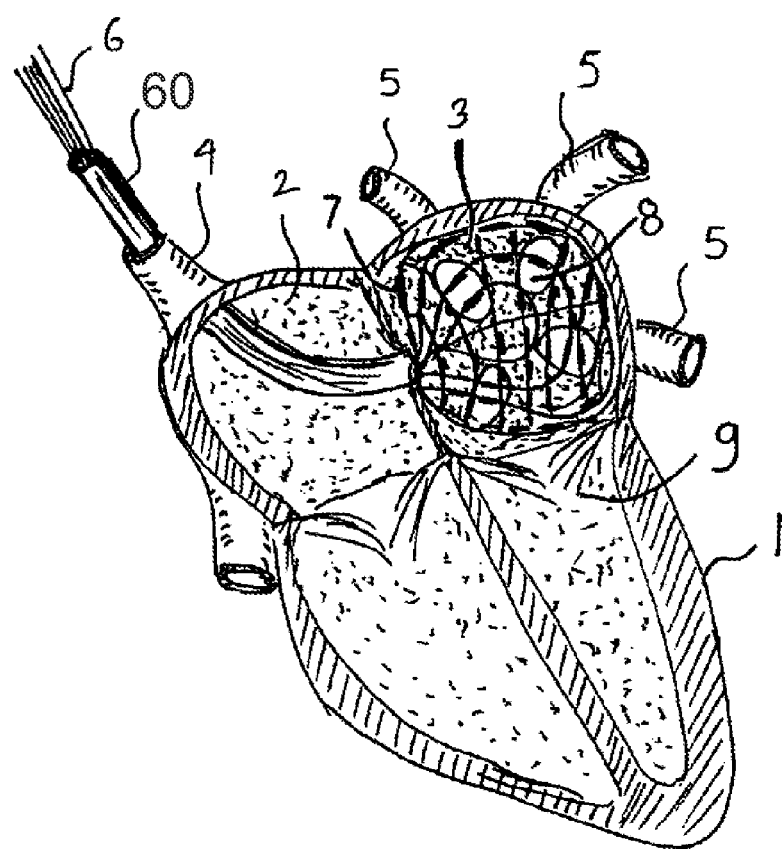
FIG. 1 is a cross sectional view of the heart showing the mapping mesh deployed in the left atrium.

FIG. 1 shows a sensing and ablation mesh 7 inserted into a left atrium 3 of a heart 1 according to one illustrated embodiment.

By way of example, the mesh 7 may be delivered via a catheter 60 inserted via a superior vena cava 4 and penetrating a transatrial septum from a right atrium 2 of the heart 1. The mesh 7 is communicatively coupled to the rest of the system, for example, by electrical wires 6.

Before any ablation takes place, the inside of the left atrium 3 is mapped in order to locate the openings or ports 8 leading to the pulmonary veins 5, as well as the mitral valve 9. A typical Maze procedure ablates a "fence" around openings or ports 8 to stop propagation of spurious electrical signals which cause the heart 1 to contract at the wrong times.

The mapping may locate some or all of the openings or ports 8 through which blood flows in and out of the left atrium 3, as the Maze procedure is mainly concerned with the location of these openings or ports 8. By the way of example, in the left atrium 3, the four openings or ports 8 leading to the pulmonary veins 5 as well as the mitral valve 9 may be located. The location of these openings or ports 8 may be based on the fact that the convective cooling effect of the blood is significant, and a slightly heated mesh 7 pressed against the walls of the left and/or right atrium 3, 2 will be cooler at the areas which are spanning the openings or ports 8 carrying blood.

Figure 2:
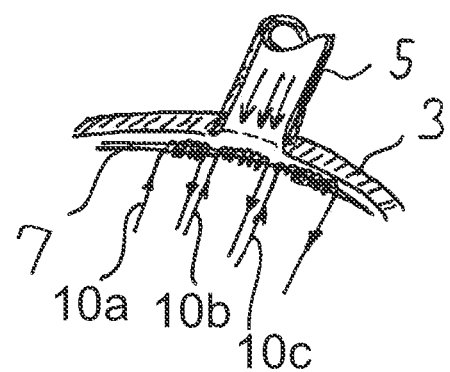
FIG. 2 is a cross sectional view of the sensing device.

FIG. 2 shows the ablation mesh 7 covered by miniature heating and/or temperature sensing elements 10a-10c flow (collectively 10, only three illustrated in the figure). Each one of these elements 10a-10c comprises a few turns of a resistive wire, for example nickel wire, wound on an electrically insulated mesh. A low current is passed through each element 10, raising a temperature of the element 10 by about 1 degree C. above normal blood temperature. A first element 10b, which lies across an opening or port 8 of one of the pulmonary veins 5, will be cooled by blood flow. The other elements are against a wall 3 and hence do not lie across any of the openings or ports 8.

By identifying the relatively cooler elements 10a, 10c on the mesh 7, the location of the openings or ports 8 may be found.

This method does not require intimate contact with the wall 3, as the cooling effect is significant even a few millimeters away from the opening.

The same elements 10 can be used as ablation electrodes during an ablation stage. It was found that the power required to raise the temperature of the mesh 7 by a small but easily detectable amount is very small, on the order of 10-50 mW per element 10. If the elements 10 are made of a material that has a significant change in resistance with temperature, the temperature drop can be sensed by measuring a voltage across the element 10 when driven by a constant current. A good choice for element material is nickel wire, which is inert, highly resistive and has a significant temperature coefficient of resistance (about 0.6% per deg C.). Since the resistance of the elements 10 is low (typically 0.1-1 ohm), the electrical noise is very low and temperature changes as low as 0.1 deg can be easily detected. For even higher detection sensitivity, the voltage waveform can be sampled in synchronization with the heart rate or the average voltage removed and only the change amplified. Such methods are referred to as "AC coupling". A further refinement to reduce the electrical noise is to pass the signal through a digital band pass filter having a center frequency tracking the heart rate. To avoid any potential tissue damage, the temperature of the elements 10 of the mesh 7 is only slightly above the blood temperature, typically 0.1-3 degrees C. above blood temperature.

Figure 3A:
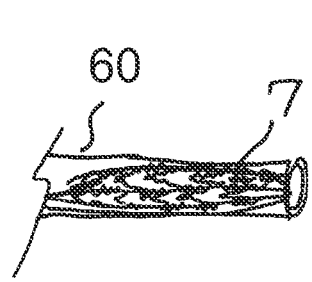
FIGS. 3A and 3B are isometric views of the mesh in both folded and expanded position.
Figure 3B:
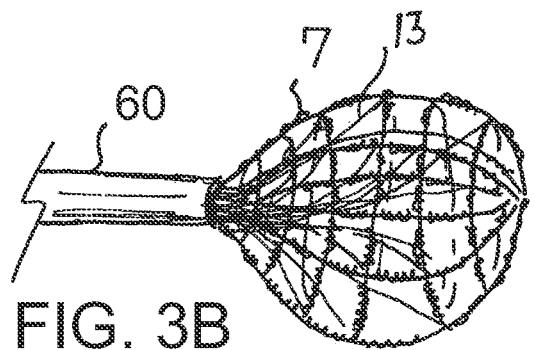

FIG. 3A shows the mesh 7 in a compressed configuration "A" and FIG. 3B shows the mesh 7 in an expanded configuration "B". Since the mesh 7 has to fit into a catheter 60, the mesh 7 should be very flexible. Besides elements 10 discussed earlier, there is also a large number of leads 13 coming out of the mesh 7. Leads 13 can be loose, as shown in FIG. 3B, or may be bonded to the mesh 7. To avoid feeding a large number of wires all the way to an operating console, an electronic selector switch may be employed, which may, for example, be mounted in the catheter 60. This reduces the number of electrical wires from over 100 to about 10. The mesh 7 can be self-expanding (elastic) or balloon-expandable. Self expanding allows normal blood flow during the procedure. For balloon expandable devices, the expansion balloon should be removed before the mapping, to avoid blocking the flow of blood.

Figure 4:
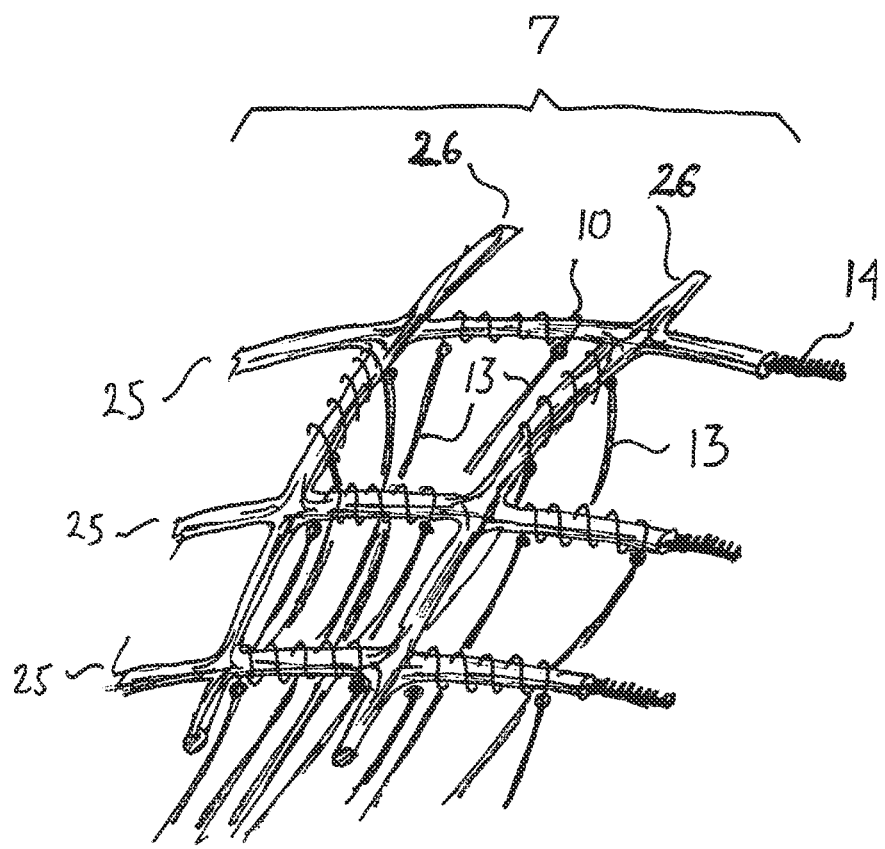
FIG. 4 is an isometric enlarged view of a portion of the mesh.

FIG. 4 shows the mesh 7 in more detail. Insulated longitudinal (i.e., parallel to catheter) wires 25 are crossed by cross wires 26. Each section of the mesh 7 is covered by a few turns of thin (0.05-0.2 mm) nickel wire 10 having leads 13. The leads 13 can be regular thin copper wire. The longitudinal wires 25 can be stiffer than the cross wires 26, therefore can be made self-expanding by incorporating a core 14 made of coiled flexible metal wire such as Nitinol. A metallic core may interfere with the ablation process at higher frequencies and can be replaced by simply making the longitudinal wires 25 of a polymeric material thicker than the cross wires 26. The cross wires 26, which may form rings around wires 25, should be very flexible to compress into the catheter 60. The cross wires 26 could incorporate a very thin wire or coiled up wire. Use of a flexible mesh 7 not only allows percutaneous delivery, but also permits the mesh 7 to follow the atrial volume change each heartbeat. The mesh 7 should stay in contact with or close to the atrial wall during the cardiac cycle, otherwise the measurement and the ablation may only be performed during parts of the cardiac cycle. The diameter of the longitudinal wires 25 and cross wires 26 are typically 0.2-1 mm. The mesh 7 may include about 10-20 longitudinal wires 25 and about 10-20 cross wires 26. The insulation can be any polymeric material such as thin enamel or polymer coating. Practically any polymer can be used, as the maximum temperature it will be subject to, including during the ablation phase, is around 100 degrees C.

Figure 5:
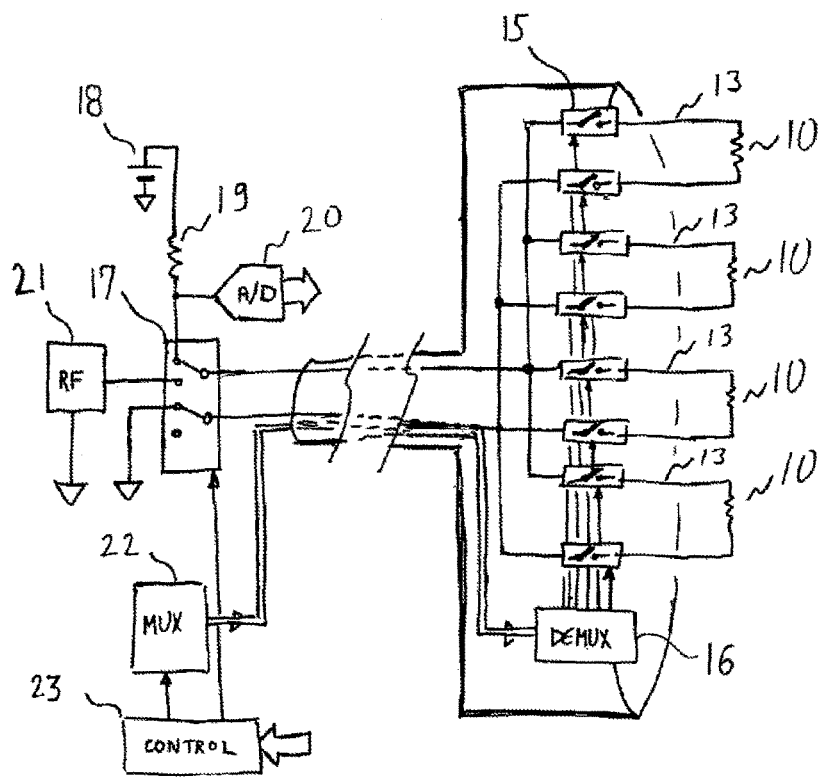
FIG. 5 is an electrical schematic of a mapping and ablation system.

FIG. 5 shows an electrical system, according to one illustrated embodiment. The elements 10 may be resistive heaters wound on the mesh 7. Each of the elements 10 is connected by electronic element switches 15 (typically FET or MOS-FET type) to a single pair of wires leading out of the body to a mode selection switch 17. Element switches 15 are selected by de-multiplexer or selector 16. The de-multiplexer or selector 16 is controlled by a small number of wires or even a single wire if data is sent in serial form, by a multiplexer 22. Element switches 15 and de-multiplexer or selector 16 may be built into the catheter 60, which may, for example, be located near the point of deployment of the mesh 7. The element switches 15 have to carry significant power during the ablation phase.

The mode selection 17 selects between a mapping mode (position shown in the drawing) and an ablation mode (second position of switch). In the mapping mode, a current is created by a voltage source 18 and resistor 19 (e.g., forming a constant current source) and routed into a selected element 10 by the element switches 15. For each measurement, the two element switches 15 that are connected to the scanned element 10 are in an enabled state (ON), the rest of the element switches being in a disabled state (OFF). The voltage drop across an element 10 is measured by an analog to digital (A/D) converter 20 and fed to a control computer 23. For greater accuracy, four terminal sensing can be employed. In a preferred embodiment, the detection is AC coupled, therefore the DC voltage drops along the wires are of no consequence, and no four-terminal sensing is needed. For AC coupling, the control computer 23 may include a 0.5 Hz low pass filter, which may be implemented in software. The slight disadvantage of the AC coupled method approach is speed, as the low signal frequency (e.g., about 1 Hz), requires a few seconds per measurement. Other temperature sensors and/or approaches, such as thermistors or thermocouples, can be used in conjunction with the elements 10. Mapping is achieved by turning on all of the elements 10 (e.g., sequentially) and measuring the temperature of each. A map may be formed in the control computer 23 and the lower temperature spots on the mesh correspond to the openings or ports 8 leading to the veins or valves.

When the mode selection switch 17 is in the ablation mode, a generator 21 (e.g., Radio Frequency (RF)) is connected (e.g., sequentially) to selected elements 10 by the control computer 23 addressing the multiplexer 22 which controls the element switches 15 via the de-multiplex selector 16. The complete operation, including scanning and ablation, can be completed in less than 5 minutes. The configuration illustrated in FIG. 5 implies unipolar ablation; however bipolar ablation can be used as well and is discussed below. Clearly other sources of ablation can be used besides RF. Frequencies from DC to microwaves can be used, as well as delivery of laser power via optical fibers or cryogenics via thin tubes. For laser ablation element switches 15 are optical switches, while for cryogenic ablation the element switches 15 are valves, and in some embodiments may take the form of heated elements such as resistive wires.

Figure 7:
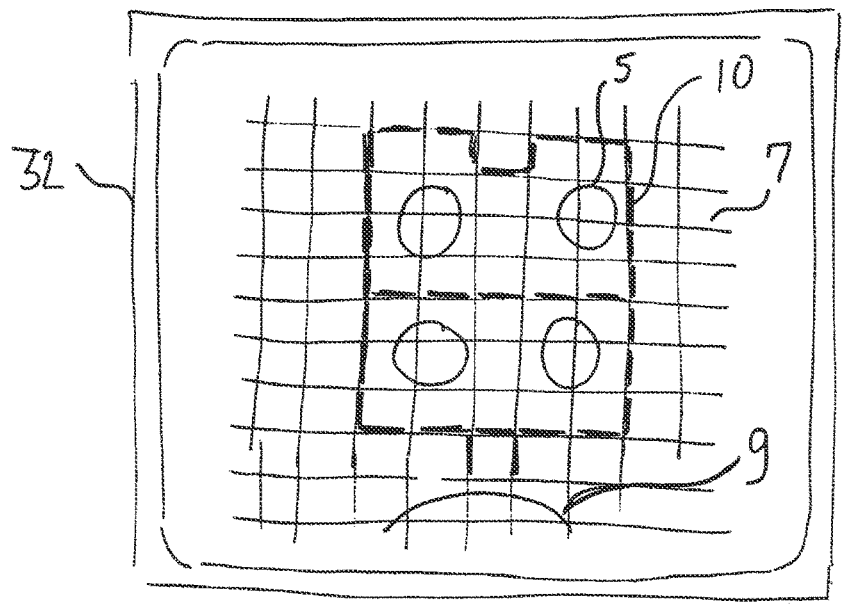
FIG. 7 is a schematic view of the display console of the system.

During ablation it is desirable to monitor the temperature of the mode selection switch 17 to the mapping position several times during the ablation procedure. The measured temperatures can be displayed on a display 32 (FIG. 7). RF ablation is typically performed at frequencies of 100 KHz-1 MHz and power levels which depend on the size of the elements 10, but can be as high as 100 W. Various RF ablation techniques and equipment are well known in the art.

Figure 6:
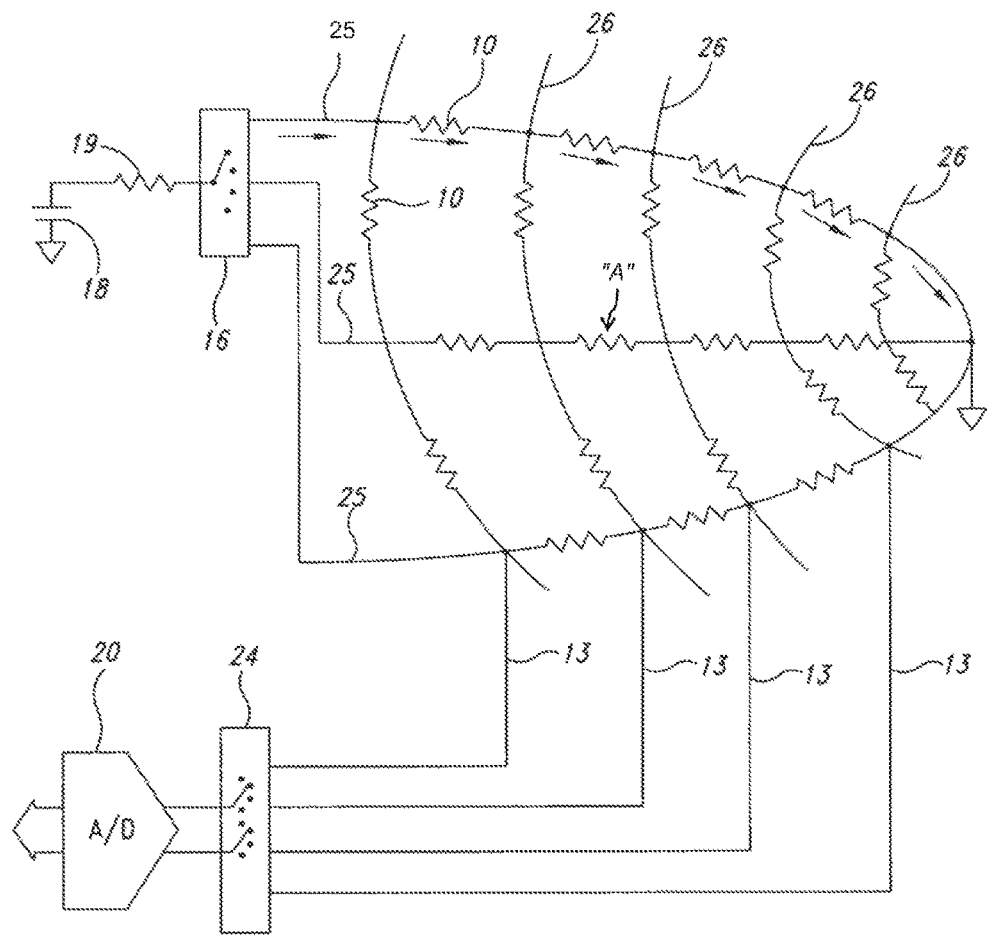
FIG. 6 is an electrical schematic of a simplified mapping system.

FIG. 6 shows an embodiment in which the mapping system is separate from the ablation system. In this system, the mesh 7 has very few connecting wires. As illustrated, each longitudinal wire 25 has a single output wire and each cross wire 26 has a single output wire 13. For a 10×10 mesh 7 with 100 nodes, only twenty-one wires are needed (ten plus ten plus ground wire), instead of two hundred wires. This allows all wires to be brought directly out of the catheter 60. This also allows placement of selector switches 16 and 24 together with the control system. For example, if the element marked as "A" is selected; a current is selected to run through the longitudinal wire 25 which includes element A. The voltage drop is sensed by the two circumferential wires 13 that connect directly to A. Since no current flows in the other elements at the time of measurement, the voltage drop is only caused by element A. It is sensed by A/D converter 20 via double pole selector 24.

After a map is established, it is displayed on a display screen 32 as shown in FIG. 7. The surgeon can select which elements 10 will cause tissue ablation in the atrium. The pattern formed is along the line of the standard Maze procedure. The location of the pulmonary veins 5 and the mitral valve 9 is inferred from the temperature date and drawn on the display screen.

Figure 8A:
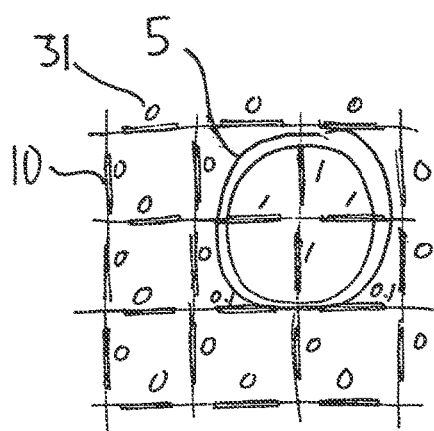
FIGS. 8A and 8B are graphical views of a mapping that illustrate an interpolation principle.
Figure 8B:
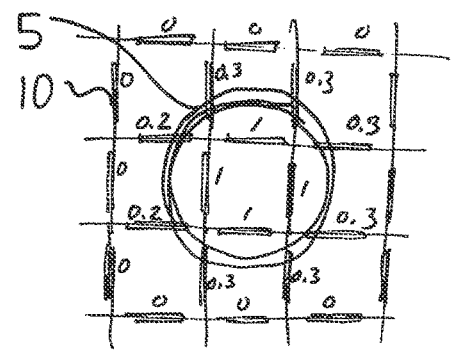

FIGS. 8A and 8B demonstrate the principle of accurate location of the veins and valves even if the grid is relatively coarse. The exact location can be interpolated based on the fact that when only part of the element 10 is exposed to the blood flow. By the way of example, if the temperature of the mesh 7 is 1 degree C. above blood temperature and equals the blood temperature under normal blood flow (this was experimentally verified), the temperatures of a group of elements 10 will be as shown in FIG. 8A when aligned with the opening or port 8 of vein 5. The number near each element 10 is the temperature drop. When moved, some of the elements 10 will only be partially positioned in the flow path under vein 5, as shown by FIG. 8B. The temperatures of those elements 10 will be between 0 and 1 degree above blood temperature. The exact temperature drop between 0 to 1 corresponds with the exact shift. This allows accurate determination of the location and size of each opening or port 8, data used by the control computer 23 to draw the map shown in FIG. 7. A grid spacing of 10 mm allows about 1 mm accuracy.

Figure 9:
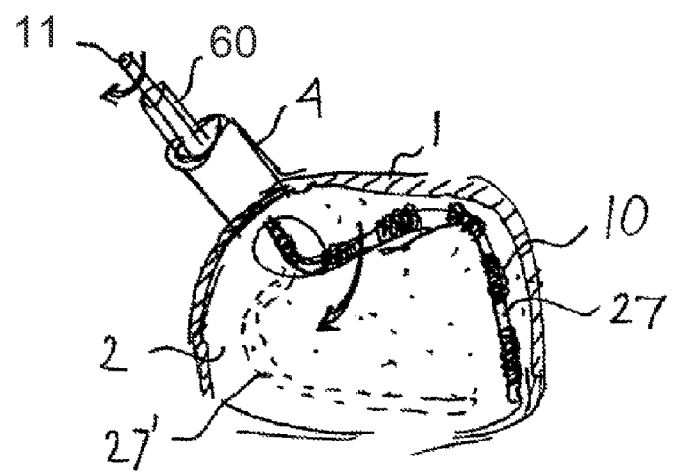
FIG. 9 is a cross sectional view of an alternate embodiment, using mechanical or manual scanning in one axis.

An alternative to a full mesh is a partial mesh, or even a single sensor, that is mechanically scanned across the area to be mapped. FIG. 9 shows a linear sensor array 27 pushed into the atrium 2 via vein 4 by the catheter 60. The linear sensor array 27 has a linear array of elements 10 similar to those used in the full mesh 7. After a linear mapping is performed the linear sensor array 27 is rotated (as shown by broken line 27') a small amount (10-20 degrees) by stem 11 (similar to electrical wires 6) and a new scan is performed. The same procedures previously described may be used for ablation.

Figure 10:
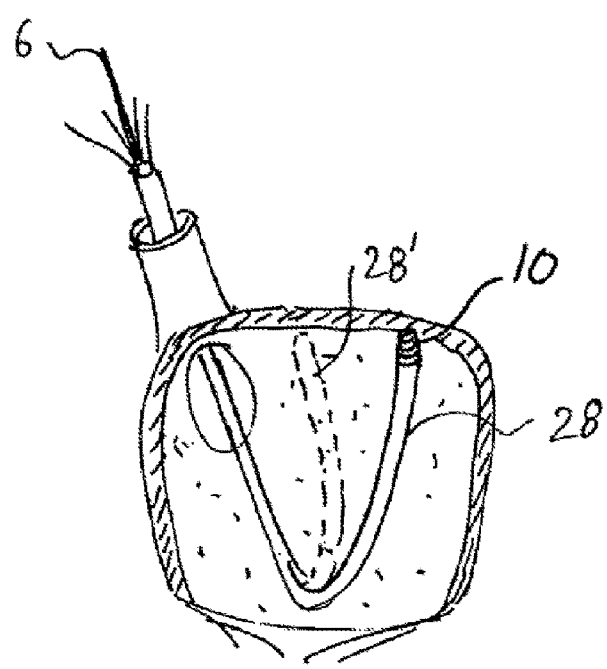
FIG. 10 is a cross sectional view of an alternate embodiment, using mechanical scanning in two dimensions.

FIG. 10 shows the use of a single steerable catheter 28 as a mapping and ablation tool. Steerable catheters are controlled remotely by mechanical, magnetic, hydraulic or other means. A steerable catheter 28 can be used to scan the inside of the atrium 3 by bending, as shown in broken line 28'. The location is monitored by external or internal sensors. A position of a tip of the steerable catheter 28 can also be monitored by fluoroscopy. The catheter tip contains a heating and/or ablation element 10. Steerable catheters 28 may advantageously carry a wide range of ablation systems, since only one connection and one point is needed.

A full mesh trades a higher complexity for better speed and accuracy when compared to linear arrays or single point scanning.

Figure 11:
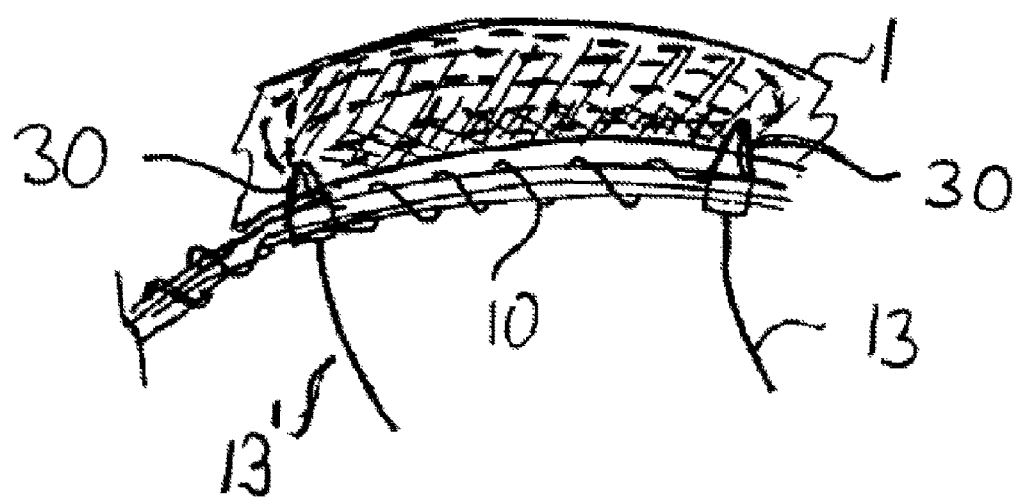
FIG. 11 shows the use of the invention for bipolar ablation.

The previous examples were of unipolar ablation, with the ablation current returning to ground via the patient's body. The disclosed system can also be used for bipolar ablation as shown in FIG. 11. In unipolar ablation the same voltage is connected to both leads 13 and 13' of an element 10. In bipolar abalation the voltage is connected to lead 13 while the other end, 13', is grounded. It is important that the element 10 will be of sufficient resistance to cause most of the ablation current to flow through heart tissue 1. Electrodes 30 make contact with tissue 1 while the wire used in the element 10 is covered by an insulator. The advantage of bipolar ablation is better control of ablation depth. Typical ablation temperatures are 60-80 degrees C. At a higher temperature the tissue 1 becomes less conductive, forcing the ablation current to seek a new path. This promotes full ablation of the tissue 1. The element 10 can also be designed to assist ablation by creating heat when ablation voltage is applied across it.

One possible advantage of at least some of the presently disclosed embodiments over electrical potential mapping methods is that the presently disclosed embodiments do not require perfect contact between the mesh 7 and the tissue 1. The presently disclosed embodiments may also advantageously be less sensitive to the surface properties of the tissue, such as scar tissue or plaque.

If the mesh is separated from the tissue by a thin layer of blood, both the temperature sensing and the ablation functions of the presently disclosed embodiments will still function properly.

The word "element" in this disclosure has to be interpreted in a broad sense as any element capable of sensing blood flow. Clearly the elements do not need to be heaters, as cooling elements will work equally well. If a material is injected into the blood flow, any sensor capable of detecting this material can be used to detect blood flow. By the way of example, if the blood is cooled or warmed slightly before returning to the heart only temperatures sensors are needed. Since temperature differences as low as 0.1 degree C. can be detected reliably, it is fairly simple to heat or cool the blood slightly before it returns to the heart (even by a simple external pad).

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art.

The various embodiments described above can be combined to provide further embodiments. All of the U.S. patents. U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A system comprising:
a plurality of sensing elements configured at least to sense blood flow;
a control computer coupled to the plurality of sensing elements, the control computer configured at least to:
receive, from the plurality of sensing elements, blood flow signals indicative of blood flow in a bodily cavity; and
identify, based at least on the received blood flow signals, a location of a structure in the bodily cavity in a map of at least a portion of the bodily cavity, the map including visual representations indicating the blood flow.

2. The system of claim 1, wherein the received blood flow signals are indicative of sensed temperature.

3. The system of claim 1, wherein the received blood flow signals are indicative of convective heat transfer by the blood flow.

4. The system of claim 1, further comprising a source coupled to at least a first one of the plurality of sensing elements to provide electric current thereto, the electric current sufficient to cause heating of at least a portion of the first one of the plurality of sensing elements, wherein the control computer is configured at least to identify the location of the structure in the bodily cavity based at least on sensing of electrical resistance of the heated portion of the first one of the plurality of sensing elements.

5. The system of claim 1, wherein the control computer is communicatively coupled to a display to cause the map to be displayed by the display.

6. The system of claim 5, wherein each sensing element of the plurality of sensing elements is responsive to convective heat transfer to sense the blood flow, and wherein the control computer is configured at least to cause the display to generate, within the displayed map, one or more visual representations indicating one or more regions of a wall of the bodily cavity and one or more visual representations indicating one or more ports in a surface of the wall of the bodily cavity based at least on the sensed blood flow.

7. The system of claim 1, wherein the map includes visual representations indicating the plurality of sensing elements, and wherein each visual representation of at least some of the visual representations indicating the blood flow is visually represented in correspondence with a respective one of the visual representations indicating the plurality of sensing elements.

8. The system of claim 1, wherein the map includes visual representations indicating the plurality of sensing elements, and wherein each visual representation of at least some of the visual representations indicating the blood flow is visually represented adjacent a respective one of the visual representations indicating the plurality of sensing elements.

9. The system of claim 1, wherein the map includes visual representations indicating the plurality of sensing elements.

10. The system of claim 9, wherein the map includes one or more visual representations indicating one or more regions of a wall of the bodily cavity and one or more visual representations indicating one or more ports in a surface of the wall of the bodily cavity based at least on the sensed blood flow.

11. The system of claim 10, wherein the map includes at least part of at least one of the visual representations indicating the plurality of sensing elements within one of the one or more visual representations indicating one of the one or more ports.

12. The system of claim 9, wherein at least some of the visual representations indicating the plurality of sensing elements are arranged in a grid pattern.

13. The system of claim 10, wherein the location of the structure in the bodily cavity is indicated at least in part by relative positioning of the visual representations indicating the plurality of sensing elements and the one or more visual representations indicating the one or more ports.

14. A system comprising:
a control computer configured at least to:
cause display of a first visual representation indicating an interior tissue surface of a bodily cavity, the first visual representation including a representation indicating the interior tissue surface interrupted by at least two ports in fluid communication with the bodily cavity; and
cause display of a second visual representation indicating at least part of a structure, the structure percutaneously deliverable to the bodily cavity,
wherein the control computer is configured at least to identify, based at least on information indicative of blood flow in the bodily cavity, a location of the structure in the bodily cavity at least by causing display of a relative alignment between at least a portion of the first visual representation and at least a portion of the second visual representation.

15. A system comprising:
a control computer configured at least to:
cause display of a distribution of data points indicative of blood flow proximate each location of a plurality of locations in a bodily cavity, wherein spatial relationships between the data points of the displayed distribution are consistent with spatial relationships between the plurality of locations in the bodily cavity; and
cause display of a visual representation indicating an interior tissue surface of the bodily cavity based at least on the distribution of the data points, the visual representation including a representation indicating the interior tissue surface interrupted by at least two ports in fluid communication with the bodily cavity.

* * * * *